United States Patent [19]

Doyle

[11] 4,425,281

[45] Jan. 10, 1984

[54] COPPER OR SILVER COMPLEXES WITH FLUORINATED DIKETONES AND UNSATURATED LIGANDS

[75] Inventor: Gerald Doyle, Whitehouse Station, N.J.

[73] Assignee: Exxon Research and Engineering Co., Florham Park, N.J.

[21] Appl. No.: 282,652

[22] Filed: Jul. 13, 1981

[51] Int. Cl.$^3$ ............................ C07F 1/10; C07F 1/08
[52] U.S. Cl. ................................ 260/430; 260/438.1; 260/429 J; 549/2; 549/3; 549/6
[58] Field of Search ................ 260/430, 438.1, 429 J, 260/429 CY; 549/3; 546/2, 6

[56] References Cited

U.S. PATENT DOCUMENTS

| | | | |
|---|---|---|---|
| 2,208,253 | 7/1940 | Flenner et al. | 260/429 J |
| 3,014,939 | 12/1961 | Kluiber | 260/429 J |
| 3,272,853 | 9/1966 | Braun | 260/429 J |
| 3,429,906 | 2/1969 | Swigar et al. | 260/430 X |
| 3,700,416 | 10/1972 | Lucid | 23/312 |
| 3,804,869 | 4/1974 | Chabardes et al. | 260/429 J |
| 4,150,047 | 4/1979 | Coe et al. | 260/429 J |
| 4,279,874 | 7/1981 | Doyle | 423/246 |

OTHER PUBLICATIONS

Belford et al., Reactions of 1,4-Diazabicyclo [2.2.2] octane with Bis-(1,1,1,5,5,5,-hexafluoropentane-2,4-dionato)Cu(II), J.C.S. Dalton, 2208 (1972).

Bailey et al., Ternary Complexes of Cu(II) with Mixed Acetylacetonate and Nitrogen-containing Ligands, J.C.S. Dalton, 984 (1980).

Partenheimer and Johnson, "The Syntheses of Some New Silver Olefin Compounds of the Type (Olefin) (β-diketonato)silver(I)", Inorganic Chemistry, 11, 2840-2841 (1972).

Primary Examiner—Helen M. S. Sneed
Attorney, Agent, or Firm—James H. Takemoto; Robert J. North

[57] ABSTRACT

A composition of matter of the formula

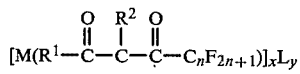

where M is Cu(I) or Ag(I); $R^1$ is $C_1-C_6$ fluoroalkyl, $C_1-C_8$ alkyl, $C_4-C_6$ heterocycle containing O, S or N or $C_6-C_{10}$ aryl; $R^2$ is H or $C_1-C_6$ alkyl, with the proviso that $R^1$ and $R^2$ together with the carbons to which they are attached may be joined together to form a $C_6$ ring; L is an unsaturated hydrocarbon containing at least one non-aromatic unsaturation; x and y are 1 or 2; and n is from 1 to 8.

15 Claims, No Drawings

COPPER OR SILVER COMPLEXES WITH FLUORINATED DIKETONES AND UNSATURATED LIGANDS

BACKGROUND OF THE INVENTION

This invention relates to new copper or silver complexes containing a fluorinated diketonate and unsaturated hydrocarbons as ligands. More particularly, copper or silver in the +1 formal oxidation state form complexes with fluorinated beta-diketonates and unsaturated ligands containing at least one nonaromatic unsaturation.

It is known that certain silver(I) and copper(I) salts form complexes with olefins and acetylenes. For example, cuprous chloride is known to form complexes with both ethylene and acetylene. U.S. Pat. No. 3,401,112 teaches a method of separating a mixture of hydrocarbons having differing degrees of unsaturation using a copper(I) salt of the formula CuXA where XA is an anion, X is oxygen or fluorine and A is the remainder of the anion. Examples of fluorinated anions include fluoro substituted carboxylates, fluorosulphonate, perfluoroborate, hexafluorophosphate and hexafluoroantimonate. CuXA forms a cuprous complex with said unsaturated hydrocarbon. Similarly, U.S. Pat. No. 3,517,079 describes a process for separating vinyl aromatic hydrocarbons from alkyl aromatic hydrocarbons using a cuprous fluoroborate or cuprous fluorophosphate salt wherein a complex is formed. U.S. Pat. Nos. 3,754,047 and 3,755,487 relate to a process for separating complexible ligands such as olefins, acetylenes, aromatics, CO and the like from feedstreams by contacting the feedstream with a cuprous salt including $CuBF_4$, $CuPF_6$ and $CuOOCCF_3$.

SUMMARY OF THE INVENTION

It has been discovered that copper(I) and silver(I) can form a new class of complexes with fluorinated acetylacetonate anions and unsaturated hydrocarbons as ligands. The complexes of the invention have the formula

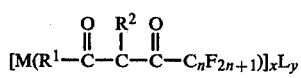

where M is Cu(I) or Ag(I); $R^1$ is $C_1$-$C_6$ fluoroalkyl, $C_1$-$C_8$ alkyl, $C_4$-$C_6$ heterocycle containing O, S or N or $C_6$-$C_{10}$ aryl; $R^2$ is H or $C_1$-$C_6$ alkyl with the proviso that $R^1$ and $R^2$ together with the carbons to which they are attached may be joined together to form a $C_6$ ring; L is an unsaturated hydrocarbon ligand containing at least one non-aromatic unsaturation capable of forming a Cu-L bond, preferably an unsaturated hydrocarbon containing at least one ethylenic, acetylenic or isonitrilic unsaturation; x and y are 1 or 2; and n is an integer from 1 to 8.

DETAILED DESCRIPTION OF THE INVENTION

The present Cu(I) complexes contain fluorinated acetylacetonate anions and unsaturated hydrocarbons as ligands. Preferred fluorinated acetylacetonate anion ligands have the formula

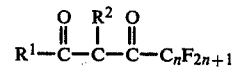

where $R^1$ is $C_1$-$C_3$ fluoroalkyl, especially $CF_3$, $C_1$-$C_6$ alkyl, $C_6$-$C_{10}$ aryl or $C_4$-$C_5$ heterocycle containing O, S or N, $R^2$ is H with the proviso that $R^1$ and $R^2$ may join together to form a $C_6$ ring, and n is an integer from 1 to 4, especially 1. Examples of neutral preferred embodiments of fluorinated acetylacenates incorporated into the present complexes as anions include

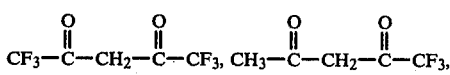

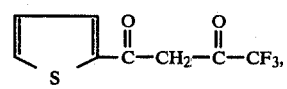

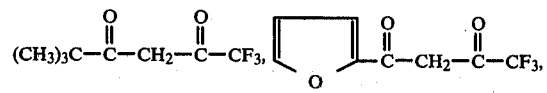

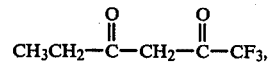

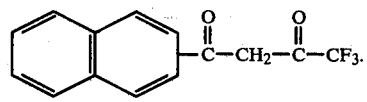

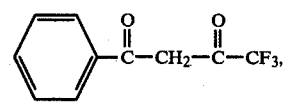

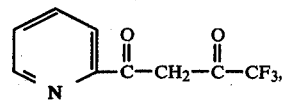

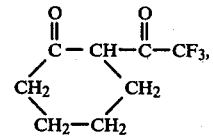

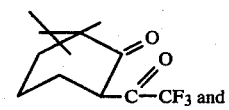

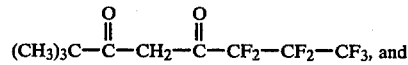

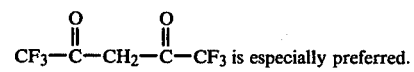

Preferred unsaturated hydrocarbons are (a) alkenes of the formula

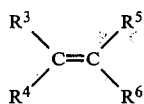

where each $R^3$-$R^6$ is independently H; $C_1$-$C_{30}$, more preferably $C_1$-$C_{15}$ and especially $C_1$-$C_8$ aliphatic with the proviso that any combination of $R^3$, $R^4$, $R^5$ and $R^6$ may be joined together to form at least one $C_4$-$C_{14}$, more preferably $C_5$-$C_{12}$, most preferably $C_6$-$C_8$ cycloaliphatic ring; —C≡N; $C_6$-$C_{10}$ aryl; $C_7$-$C_{14}$ araliphatic;

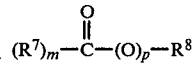

where m and p are 0 or 1, $R^7$ is $C_1$-$C_{20}$, preferably $C_1$-$C_{10}$ aliphatic, and $R^8$ is H, $C_1$-$C_{10}$ aliphatic or $C_6$-$C_{10}$ aryl with the proviso that adjacent

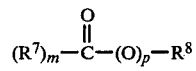

may be joined together to form a $C_4$-$C_{16}$ anhydride; (b) alkynes of the formula $R^9$—C≡C—$R^{10}$ where $R^9$ and $R^{10}$ are independently H; $C_1$-$C_{30}$, more preferably $C_1$-$C_{15}$ and especially $C_1$-$C_8$ aliphatic; $C_6$-$C_{10}$ aryl or $C_7$-$C_{14}$ araliphatic; or (c) isonitriles of the formula $R^{11}$—N≡C where $R^{11}$ is $C_1$-$C_{20}$ aliphatic; $C_3$-$C_{10}$ cycloaliphatic; $C_7$-$C_{20}$ araliphatic or $C_6$-$C_{10}$ aryl. The unsaturated hydrocarbons may be substituted with unreactive substituents such as halogen, cyano, alkoxy, nitro, and the like.

Examples of suitable unsaturated ligands include: ethylene, acetylene, 1-octene, isobutylene, 1,5-cyclooctadiene, stilbene, diphenylacetylene, styrene, cyclooctene, 1,5,9-cyclododecatriene, 1,3-hexadiene, isopropylacetylene, 1-decene, 2,5-bicycloheptadiene, 1-octadecene, cyclopentene, octalin, methylene cyclohexane, diphenyl fulvene, 1-octadecyne, benzyl cinnamate, benzal acetophenone, acrolein, acrylonitrile, maleic anhydride, oleic acid, linolenic acid, acrylic acid, methyl methacrylate and diethyl maleate. Suitable isonitriles are, e.g., methyl isocyanide, butyl isocyanide, cyclohexyl isocyanide, phenylethyl isocyanide and phenyl isocyanide.

Examples of copper(I) and silver(I) complexes are as follows.

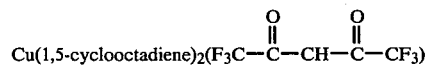

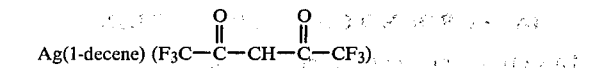

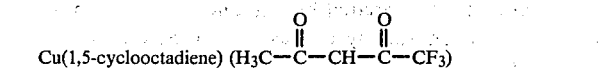

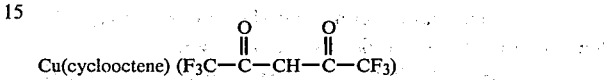

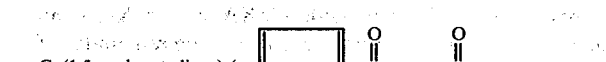

The complexes of the invention may be prepared by reacting metal oxide, fluorinated acetylacetone and unsaturated ligand in an inert organic solvent. The preparation of a cuprous complex is illustrated by the following equation:

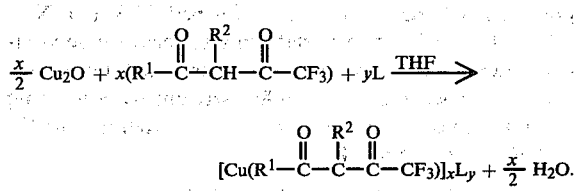

Silver(I) complexes are similarly prepared. Reactants are preferably combined in approximately stoichiometric amounts. The amounts, however, are not critical and variations therefrom are possible. The reaction preferably takes place in an inert organic solvent. Preferred solvents are ethers, ketones, esters, alcohols, saturated aliphatic hydrocarbons, aromatic hydrocarbons and the like. It is necessary that the amount of CO in the reaction mixture not exceed about 10 vol%. In the above preparative reaction, CO competes with unsaturated ligand in the formation of cuprous complex and based on thermodynamic considerations, a CO complex forms in preference to the unsaturated ligand complex as long as competing amounts of CO are present. It is also desirable to carry the preparative reaction in an inert atmosphere, since gases such as oxygen may result in the oxidation of Cu(I) to Cu(II). Complexes according to the invention may also be prepared by the following reaction schemes:

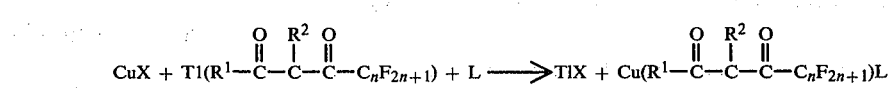

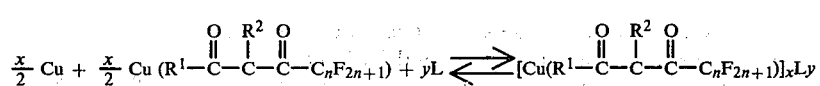

-continued-

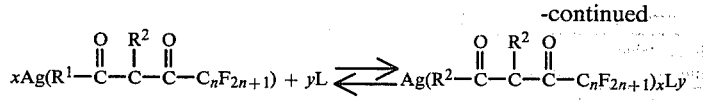

$$x\text{Ag}(R^1-\overset{O}{\underset{\|}{C}}-\overset{R^2}{\underset{|}{C}}-\overset{O}{\underset{\|}{C}}-C_nF_{2n+1}) + yL \rightleftarrows \text{Ag}(R^2-\overset{O}{\underset{\|}{C}}-\overset{R^2}{\underset{|}{C}}-\overset{O}{\underset{\|}{C}}-C_nF_{2n+1})_xL_y$$

Reaction times are not critical. Generally, the reaction mixture is stirred until a clear solution is obtained. A solid product may then be isolated by evaporating solvent. Suitable temperatures are from about $-100°$ to $+100°$ C. with room temperature being preferred. If the reaction mixture is heated excessively, it is possible that a dissociative reaction may take place, leading to a decrease in yield. Thus, copper(I) ethylene complexes are rather unstable due to a high dissociative pressure and heating would not be desirable. On the other hand, higher molecular weight olefins result in stable compounds, and the reaction mixture can be heated without harmful results with respect to yields.

Copper(I) and silver(I) complexes according to the invention are useful in gas separation processes and as catalysts or catalyst precursors. The complexes are further illustrated in the following examples.

EXAMPLE 1

A suspension of 1.45 g (0.01 mole) cuprous oxide in 75 ml methylene chloride was stirred with 2.16 g (0.02 mole) of 1,5-cyclooctadiene in a 250 ml flask under nitrogen. A solution of 4.16 g (0.02 mole) 1,1,1,5,5,5-hexafluoroacetylacetone (hfacac) in 50 ml methylene chloride was added dropwise over a 30 minute period. Red $Cu_2O$ gradually dissolved forming a clear yellow solution. The solution was filtered to remove any remaining solids and the solvent was then removed on a rotary evaporator. Cu(1,5-COD)(hfacac) was obtained as bright yellow crystals which could be purified by recrystallization from hexane. The product was characterized by IR and MNR spectroscopy and elemental analysis.

EXAMPLE 2

This example illustrates the preparation of complexes using CuI, a thallium salt and unsaturated ligand. To 50 ml of $CH_2Cl_2$ was added 0.93 g CuI and 0.53 g of 1,5-cyclooctadiene (COD). After stirring for 20 minutes, 2.0 g of thallium hexafluoroacetylacetonate was added and the mixture stirred overnight. TlI was separated by filtration and the filtrate evaporated to give 1.85 g of crystalline Cu(COD) hfacac.

EXAMPLES 3-42

Using the techniques described in Example 1, other complexes were prepared as shown in the following table.

TABLE I

| Ex. No. | Ligand (mmol) | β-diketone, (mmol) | Metal Oxide (mmol) | Solvent | Compound Formed |
|---|---|---|---|---|---|
| 3 | 1,5-cyclooctadiene (COD) (9.0) | thenoyltrifluoro-acetylacetone (TTA) (14.0) | $Cu_2O$ (9.0) | $CH_2Cl_2$ | Cu (COD) TTA |
| 4 | 1,5-cyclooctadiene (20.0) | hexafluoroacetyl-acetone (hfacac) (18.0) | $Cu_2O$ (11.0) | $C_6H_5CH_3$ | Cu (COD) hfacac |
| 5 | 1,3-butadiene (large excess) | hexafluoroacetyl-acetone (14.0) | $Cu_2O$ (7.0) | THF | $Cu(C_4H_6)$ hfacac* |
| 6 | Diphenylacetylene (9.65) | hexafluoroacetyl-acetone (4.81) | $Cu_2O$ (3.0) | $CH_2Cl_2$ | $Cu(\phi C\equiv C\phi)_2$hfacac |
| 7 | Diphenylacetylene (9.65) | trifluoroacetyl-acetone (tfacac) (4.80) | $Cu_2O$ (3.0) | $CH_2Cl_2$ | $Cu(\phi C\equiv C\phi)_2$tfacac |
| 8 | 1,5-cyclooctadiene (20.0) | trifluoroacetyl-acetone (18.0) | $Cu_2O$ (11.0) | $CH_2Cl_2$ | Cu(COD) tfacac |
| 9 | Bicyclo[2.2.1]hepta-2,5-diene (22.0) | hexafluoroacetyl-acetone (21.0) | $Cu_2O$ (11.0) | $CH_2Cl_2$ | [Cu(hfacac)]₂ ⟨structure⟩ |
| 10 | cyclohexyliso-nitrile (13.0) | hexafluoroacetyl-acetone (6.0) | $Cu_2O$ (3.0) | $CH_2Cl_2$ | Cu(C≡N—⟨cyclohexyl⟩) hfacac |
| 11 | Bicyclo[2.2.1]-2-heptene (18.0) | hexafluoroacetyl-acetone (17.0) | $Cu_2O$ (11.0) | $CH_2Cl_2$ | Cu(⟨norbornene⟩)hfacac |
| 12 | 1,3,5,7-cyclo-octatetraene (7.5) | trifluoroacetyl-acetone (7.1) | $Cu_2O$ (4.0) | $CH_2Cl_2$ | Cu(COT) tfacac |
| 13 | 1,3,5,7-cyclo-octatetraene (3.6) | trifluoroacetyl-acetone (7.2) | $Cu_2O$ (4.0) | $CH_2Cl_2$ | [Cu(tfacac)]₂COT |
| 14 | 2-hexyne (5.0) | hexafluoroacetyl-acetone (4.3) | $Cu_2O$ (2.5) | $CH_2Cl_2$ | $Cu(CH_3C\equiv CC_3H_7)$ hfacac |
| 15 | styrene (11.5) | hexafluoroacetyl-acetone (9.61) | $Cu_2O$ (5.00) | $CH_2Cl_2$ | $Cu(CH_2=CH-\phi)$ hfacac |
| 16 | isoprene (15.0) | hexafluoroacetyl-acetone (7.3) | $Cu_2O$ (4.0) | $CH_2Cl_2$ | $Cu(CH_2=\underset{\underset{CH_3}{\|}}{C}-CH=CH_2)$ hfacac |

TABLE I-continued

| Ex. No. | Ligand (mmol) | β-diketone, (mmol) | Metal Oxide (mmol) | Solvent | Compound Formed |
|---|---|---|---|---|---|
| 17 | ethylene (large excess) | hexafluoroacetyl-acetone (6.9) | Cu$_2$O (3.5) | CH$_2$Cl$_2$ | Cu(CH$_2$=CH$_2$)hfacac* |
| 18 | 2,8-decadiyne (15.0) | hexafluoroacetyl-acetone (14.0) | Cu$_2$O (8.0) | CH$_2$Cl$_2$ | [Cu(hfacac)]$_2$CH$_3$C≡C—(CH$_2$)$_4$C≡CCH$_3$ |
| 19 | 1,5-cyclooctadiene (4.5) | 3-trifluoroacetyl-d-camphor (TAC) (4.0) | Cu$_2$O (2.0) | CH$_2$Cl$_2$ | Cu(COD) (TAC) |
| 20 | cyclohexene (27.0) | hexafluoroacetyl-acetone (12.0) | Cu$_2$O (7.0) | CH$_2$Cl$_2$ | 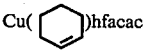 |
| 21 | Bicyclo[2.2.1]-2-heptene (14.0) | trifluoroacetyl-acetone (13.0) | Cu$_2$O (6.5) | CH$_2$Cl$_2$ | 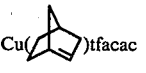 |
| 22 | cyclohexylisonitrile (16.0) | trifluoroacetyl-acetone (8.2) | Cu$_2$O (15.0) | CH$_2$Cl$_2$ | 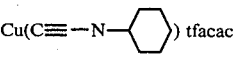 |
| 23 | phenylacetylene (15.0) | hexafluoroacetyl-acetone (15.0) | Cu$_2$O (8.0) | CH$_2$Cl$_2$ | Cu(φC≡CH) hfacac |
| 24 | cyclooctene (COE) (9.07) | hexafluoroacetyl-acetone (9.0) | Cu$_2$O (4.6) | CH$_2$Cl$_2$ | Cu(COE) hfacac |
| 25 | propene (large excess) | hexafluoroacetyl-acetone (6.9) | Cu$_2$O (3.5) | CH$_2$Cl$_2$ | Cu(CH$_3$CH=CH$_2$) hfacac* |
| 26 | 1-decene (24.0) | hexafluoroacetyl-acetone (24.0) | Cu$_2$O (14.0) | CH$_2$Cl$_2$ | Cu(CH$_2$=CH—C$_8$H$_{17}$) hfacac |
| 27 | 3-methylcyclohexene (15) | hexafluoroacetyl-acetone (9.0) | Cu$_2$O (5.0) | CH$_2$Cl$_2$ | 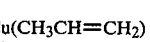 |
| 28 | 1,3,5,7-cyclooctatetraene (7.5) | hexafluoroacetyl-acetone (7.2) | Cu$_2$O (4.0) | CH$_2$Cl$_2$ | Cu(COT) hfacac |
| 29 | 1,3,5,7-cyclooctatetraene (3.6) | hexafluoroacetyl-acetone (7.2) | Cu$_2$O (4.0) | CH$_2$Cl$_2$ | [Cu(hfacac)]$_2$COT |
| 30 | (+)-α-pinene (7.5) | hexafluoroacetyl-acetone (7.4) | Cu$_2$O (4.0) | CH$_2$Cl$_2$ | Cu(α-pinene) hfacac |
| 31 | 3-methyl-cyclohexene (8.0) | 3-trifluoroacetyl-d-camphor (6.0) | Cu$_2$O (3.5) | CH$_2$Cl$_2$ | 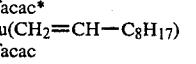 |
| 32 | d,l-α-pinene (8.0) | 3-trifluoroacetyl-d-camphor (6.0) | Cu$_2$O (3.5) | CH$_2$Cl$_2$ | Cu(d-α-pinene) TAC +Cu (l-α-pinene) TAC, mixed diastereomers |
| 33 | 1,5-cyclooctadiene (1.12) | hexafluoroacetyl-acetone (1.12) | Ag$_2$O (0.56) | CH$_2$Cl$_2$ | Ag(COD) hfacac |
| 34 | ethylene (large excess) | hexafluoroacetyl-acetone (4.28) | Ag$_2$O (2.16) | CH$_2$Cl$_2$ | Ag(CH$_2$=CH$_2$) hfacac* |
| 35 | diphenylacetylene (8.64) | hexafluoroacetyl-acetone (4.30) | Ag$_2$O (2.16) | CH$_2$Cl$_2$ | Ag(φC≡Cφ)$_2$hfacac |
| 36 | cyclooctene (8.64) | hexafluoroacetyl-acetone (8.64) | Ag$_2$O (4.37) | CH$_2$Cl$_2$ | Ag(COE) hfacac |
| 37 | propylene (large excess) | hexafluoroacetyl-acetone (4.28) | Ag$_2$O (2.16) | CH$_2$Cl$_2$ | Ag(CH$_3$CH=CH$_2$)hfacac |
| 38 | 1-decene (4.4) | hexafluoroacetyl-acetone (4.3) | Ag$_2$O (2.2) | CH$_2$Cl$_2$ | Ag(CH$_2$=CHC$_8$H$_{17}$) hfacac |
| 39 | 1,3-butadiene (large excess) | hexafluoroacetyl-acetone (4.3) | Ag$_2$O (2.16) | CH$_2$Cl$_2$ | Ag(CH$_2$=CH—CH=CH$_2$) hfacac* |
| 40 | bicyclo[2.2.1]-2-heptene (4.4) | hexafluoroacetyl-acetone (4.3) | Ag$_2$O (2.2) | CH$_2$Cl$_2$ | 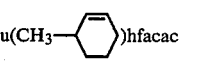 |
| 41 | bicyclo[2.2.1] hepta-2,5-diene (4.4) | hexafluoroacetyl-acetone (4.3) | Ag$_2$O (2.2) | CH$_2$Cl$_2$ | 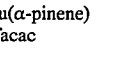 |
| 42 | diethylmaleate (100) | hexafluoroacetyl-acetone (20.0) | Cu$_2$O (10.0) | none | Cu(C$_2$H$_5$OC(=O)—CH=CH—C(=O)—OC$_2$H$_5$)hfacac |

*Not stable at room temperature.

What is claimed is:

1. A composition of matter comprising a complex of the formula

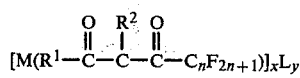

where M is Cu(I); $R^1$ is $C_1$-$C_6$ fluoroalkyl, $C_1$-$C_8$ alkyl, $C_4$-$C_6$ heterocycle containing O, S or N or $C_6$-$C_{10}$ aryl; $R^2$ is H or $C_1$-$C_6$ alkyl with the proviso that $R^1$ and $R^2$ together with the carbons to which they are attached may be joined together to form a $C_6$ ring; L is an unsaturated hydrocarbon ligand containing at least one non-aromatic unsaturation; x and y are 1 or 2; and n is from 1 to 8.

2. The composition of claim 1 wherein L is an unsaturated hydrocarbon containing at least one ethylenic, acetylenic or isonitrilic unsaturation.

3. The composition of claim 1 wherein L is an (a) alkene of the formula

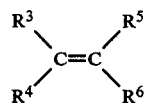

where each $R^3$-$R^6$ is independently H; $C_1$-$C_{30}$ aliphatic with the proviso that any combination of $R^3$, $R^4$, $R^5$ and $R^6$ may be joined together to form at least one $C_4$-$C_{14}$ cycloaliphatic ring; —C≡N; $C_6$-$C_{10}$ aryl; $C_7$-$C_{14}$ araliphatic;

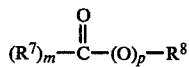

where m and p are 0 or 1, $R^7$ is $C_1$-$C_{20}$ aliphatic, $R^8$ is H, $C_1$-$C_{10}$ aliphatic or $C_6$-$C_{10}$ aryl with the proviso that adjacent

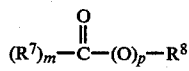

may be joined together to form a $C_4$-$C_{16}$ anhydride; (b) alkyne of the formula $R^9$—C≡C—$R^{10}$ where $R^9$ and $R^{10}$ are independently H; $C_1$-$C_{30}$ aliphatic; $C_6$-$C_{10}$ aryl or $C_7$-$C_{14}$ araliphatic; or (c) isonitrile of the formula $R^{11}$—N≡C where $R^{11}$ is $C_1$-$C_{20}$ aliphatic; $C_3$-$C_{10}$ cycloaliphatic; $C_7$-$C_{20}$ araliphatic or $C_6$-$C_{10}$ aryl.

4. The composition of claim 3 wherein L is substituted with halogen, cyano, alkoxy or nitro.

5. The composition of claim 1 wherein $R^1$ is $C_1$-$C_3$ fluoroalkyl, $C_1$-$C_6$ alkyl, $C_6$-$C_{10}$ aryl or $C_4$ or $C_5$ heterocycle containing O, S or N.

6. The composition of claim 1 wherein $R^1$ is $CF_3$ and n is 1.

7. The composition of claim 1 wherein n is 1.

8. The composition of claim 1 wherein $R^2$ is H.

9. The composition of claim 3 wherein $R^3$-$R^6$ are independently H, $C_1$-$C_{15}$ aliphatic, $C_5$-$C_{12}$ cycloaliphatic, $C_6$-$C_{10}$ aryl or $C_7$-$C_{14}$ araliphatic.

10. The composition of claim 3 wherein m is 0 and p is 1.

11. The composition of claim 3 wherein $R^1$ is $CF_3$, $CH_3$ or

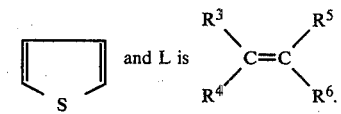

12. The composition of claim 3 wherein $R^1$ is $CF_3$, $R^2$ is H, n is 1, x and y are 1 and L is

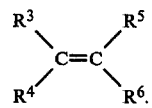

13. A composition of matter comprising a complex of the formula

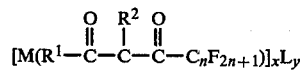

where M is Cu(I); $R^1$ is $C_1$-$C_6$ fluoroalkyl, $C_1$-$C_8$ alkyl, $C_4$-$C_6$ heterocycle containing O, S or N or $C_6$-$C_{10}$ aryl; $R^2$ is H or $C_1$-$C_6$ alkyl with the proviso that $R^1$ and $R^2$ together with the carbons to which they are attached may be joined together to form a $C_6$ ring; L is an alkene, alkyne or isonitrile; x and y are 1 or 2; and n is from 1 to 8.

14. A composition of matter comprising a complex of the formula

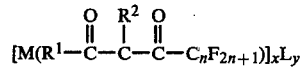

where M is Ag(I); $R^1$ is $C_1$-$C_6$ fluoroalkyl, $C_1$-$C_8$ alkyl, $C_4$-$C_6$ heterocycle containing O, S or N or $C_6$-$C_{10}$ aryl; $R^2$ is H or $C_1$-$C_6$ alkyl with the proviso that $R^1$ and $R^2$ together with the carbons to which they are attached may be joined together to form a $C_6$ ring; L is an (a) alkene of the formula

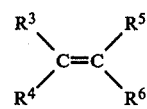

where each $R^3$-$R^6$ independently H; $C_1$-$C_{30}$ aliphatic; —C≡N; $C_6$-$C_{10}$ aryl; $C_7$-$C_{14}$ araliphatic;

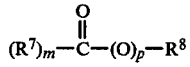

where m and p are 0 or 1, $R^7$ is $C_1$-$C_{20}$ aliphatic, $R^8$ is H, $C_1$-$C_{10}$ aliphatic or $C_6$-$C_{10}$ aryl with the proviso that adjacent

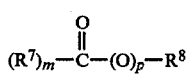

may be joined together to form a $C_4$-$C_{16}$ anhydride; (b) alkyne of the formula R—$^9$C≡C—$R^{10}$ where $R^9$ and $R^{10}$ are independently H; $C_1$-$C_{30}$ aliphatic; $C_6$-$C_{10}$ aryl or $C_7$-$C_{14}$ araliphatc; or (c) isonitrile of the formula $R^{11}-N\equiv C$ where $R^{11}$ is $C_1$-$C_{20}$ aliphatic; $C_3$-$C_{10}$ cycloaliphatic; $C_7$-$C_{20}$ araliphatic or $C_6$-$C_{10}$ aryl.

15. A method for preparing the composition of claim 1 which comprises contacting $M_2O$ where M is Cu with $$R^1-\overset{O}{\underset{\|}{C}}-\overset{R^2}{\underset{|}{CH}}-\overset{O}{\underset{\|}{C}}-C_nF_{n+1}$$

and L in an inert organic solvent and in an inert atmosphere at temperatures of from $-100°$ to $+100°$ C.

* * * * *